(12) United States Patent
Lomprey et al.

(10) Patent No.: US 6,594,066 B2
(45) Date of Patent: *Jul. 15, 2003

(54) SUBSTITUTED METALLOCENES AND ELECTROCHROMIC MEDIA AND DEVICES COMPRISING THE SAME

(75) Inventors: Jeffrey R. Lomprey, Holland, MI (US); Thomas F. Guarr, Holland, MI (US)

(73) Assignee: Gentex Corporation, Zeeland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/121,760

(22) Filed: Apr. 22, 2002

(65) Prior Publication Data

US 2003/0039020 A1 Feb. 27, 2003

Related U.S. Application Data

(63) Continuation of application No. 09/677,689, filed on Oct. 2, 2000, now Pat. No. 6,392,783.
(60) Provisional application No. 60/184,588, filed on Feb. 24, 2000.

(51) Int. Cl.[7] .............................. G02F 1/01; G02F 1/00; C07D 279/18
(52) U.S. Cl. ....................... 359/265; 359/272; 359/321; 252/583; 544/37
(58) Field of Search ................................ 359/265, 272, 359/273, 275, 321, 322; 252/583; 544/37

(56) References Cited

U.S. PATENT DOCUMENTS

| | | | |
|---|---|---|---|
| 5,724,187 A | 3/1998 | Varaprasad et al. | 359/608 |
| 5,770,114 A | 6/1998 | Byker et al. | 252/583 |
| 5,876,581 A | 3/1999 | Itaya et al. | 205/316 |
| 5,910,854 A | 6/1999 | Varaprasad et al. | 359/273 |
| 6,002,511 A | 12/1999 | Varaprasad et al. | 359/265 |
| 6,064,508 A | 5/2000 | Forgette et al. | 359/267 |
| 6,137,620 A | 10/2000 | Guarr et al. | 359/273 |
| 6,143,209 A | 11/2000 | Lynam | 252/583 |
| 6,193,912 B1 | 2/2001 | Thieste et al. | 252/583 |
| 6,392,783 B1 * | 5/2002 | Lomprey et al. | 359/265 |

FOREIGN PATENT DOCUMENTS

| | | |
|---|---|---|
| EP | 1 010 741 A2 | 6/2000 |
| SU | 830456 A1 | 2/1993 |

* cited by examiner

Primary Examiner—Georgia Epps
Assistant Examiner—Timothy Thompson
(74) Attorney, Agent, or Firm—King & Jovanovic, PLC

(57) ABSTRACT

An electrochromic device comprising at least one substantially transparent substrate having an electrically conductive material associated therewith, and an electrochromic medium which comprises a solvent, a cathodic material, and an anodic electrochromic material represented by the formula:

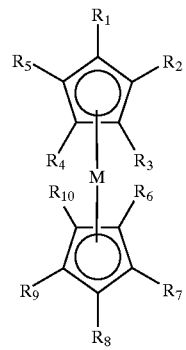

wherein $R_1$–$R_{10}$ are the same or different and at least three of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates; ketones; esters; and amides; ethers, including polyethers; amines, including tertiary amines; alkenes; alkynes; and mixtures thereof; wherein any remainder of $R_1$–$R_{10}$ comprise H; and wherein M comprises a transition metal.

46 Claims, 3 Drawing Sheets

SUBSTITUTED METALLOCENES AND ELECTROCHROMIC MEDIA AND DEVICES COMPRISING THE SAME

This application is a continuation application of U.S. application Ser. No. 09/677,689 filed on Oct. 2, 2000, now U.S. Pat. No. 6,392,783, which claims the benefit of U.S. Provisional Application Serial No. 60/184,588, filed Feb. 24, 2000, the entirety of which are hereby incorporated herein by reference.

BACKGROUND OF THE INVENTION

1. Field of the Invention

The present invention relates in general to electrochromic materials for use in electrochromic devices, and more particularly, to anodic electrochromic materials comprising substituted metallocenes.

2. Background Art

Electrochromic materials have been known in the art for several years. Furthermore, experimentation associated with the utilization of metallocenes and simple substituted metallocenes as anodic electrochromic materials has also been explored. While the utilization of such anodic electrochromic materials in electrochromic devices has been identified, they have not exhibited sufficient thermal and/or ultraviolet stability characteristics for long term use in electrochromic devices.

It is therefore an object of the present invention to provide an anodic electrochromic material comprising a substituted metallocene having constituents which substantially protect the metal center from chemical reactions that would otherwise adversely affect stability of the same.

These and other objects of the present invention will become apparent in light of the present specification, claims, and drawings.

SUMMARY OF THE INVENTION

The present invention is directed to an electrochromic device comprising: (a) at least one substantially transparent substrate having an electrically conductive material associated therewith; and (b) an electrochromic medium which comprises: (1) a solvent; (2) a cathodic material; and (3) an anodic electrochromic material represented by the formula:

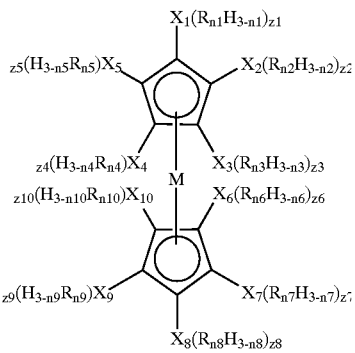

wherein M comprises a transition metal wherein $X_1$–$X_{10}$ are the same or different and. comprise C, Si, or H; wherein $R_{n1}$–$R_{n10}$ are the same or different and comprise O, C, or a straight or branched alkyl, aryl, alkaryl, or aralkyl group containing approximately 1 to approximately 40 carbon atom(s), wherein the carbon atom(s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates; ketones; esters; and amides; ethers, including polyethers; amines, including tertiary amines; alkenes; alkynes; and mixtures thereof; wherein $n_1$–$n_{10}$ are the same or different and comprise 0, 1, 2, or 3, and are the number of bonds between a given X and associated constituent(s) other than hydrogen; wherein $Z_1$–$Z_{10}$ are the same or different and comprise 0 or 1; and wherein $$\sum_{y=1}^{10} n_y \geq 7; \sum_{y=1}^{10} z_y \geq 7; \text{ or } \sum_{y=1}^{10} (n_y + z_y) \geq 9.$$

The present invention is also directed to an electrochromic device comprising: (a) at least one substantially transparent substrate having an electrically conductive material associated therewith; and (b) an electrochromic medium which comprises (1) a solvent; (2) a cathodic material; and (3) an anodic electrochromic material represented by the formula:

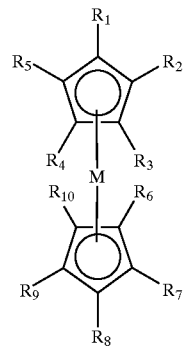

wherein $R_1$–$R_{10}$ are the same or different and at least three of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates; ketones; esters; and amides; ethers, including polyethers; amines, including tertiary amines; alkenes; alkynes; and mixtures thereof; wherein any remainder of $R_1$–$R_{10}$ comprise H; and wherein M comprises a transition metal.

Preferably some or all of constituents $R_1$–$R_{10}$ serve to increase stability of the metallocene relative to the stability of the metallocene without the constituents.

The present invention is also directed to an electrochromic medium comprising one or more solvents, one or more cathodic materials, and one or more above-identified anodic electrochromic materials.

The present invention is further directed to an electrochromic device comprising at least one substantially transparent substrate having an electrically conductive material associated therewith, and an above-identified electrochromic medium.

BRIEF DESCRIPTION OF THE DRAWINGS

The invention will now be described with reference to the drawings wherein.

DETAILED DESCRIPTION OF THE INVENTION

Figure 1:
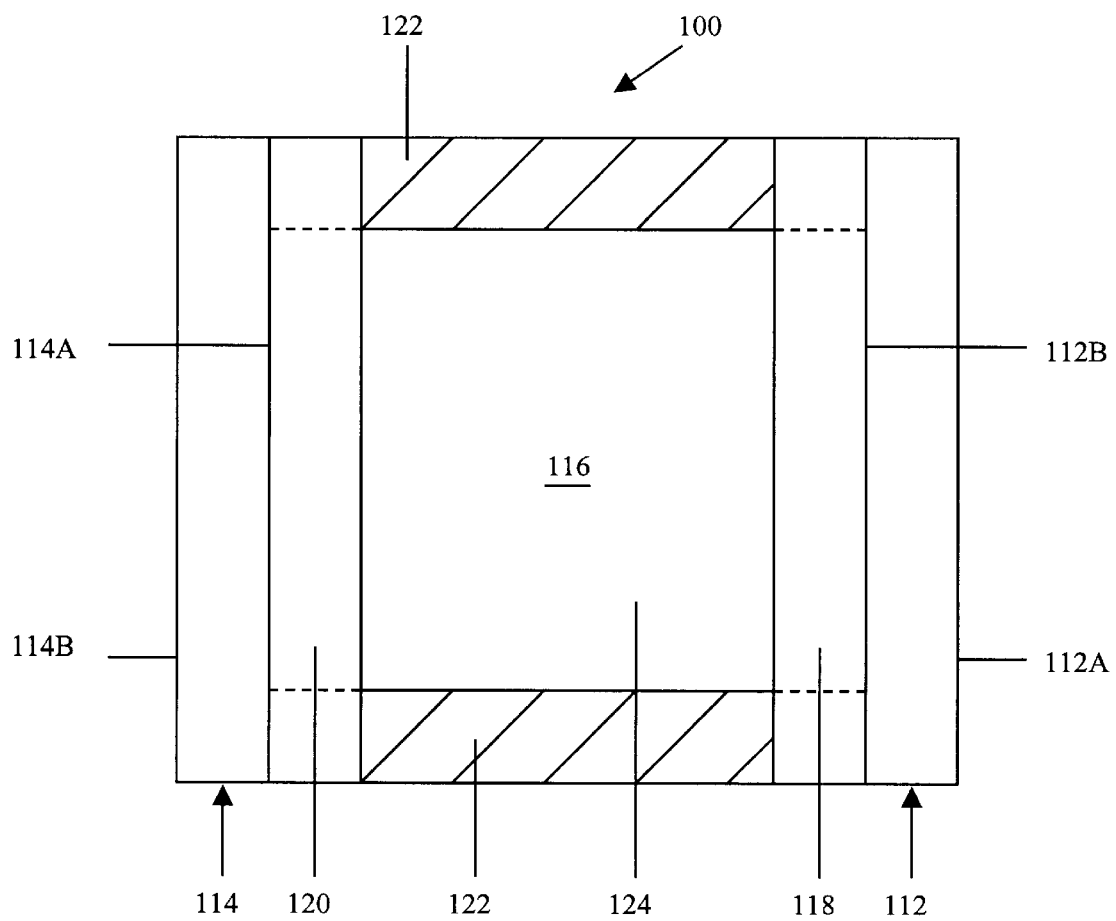
FIG. 1 of the drawings is a cross-sectional schematic representation of an electrochromic device fabricated in accordance with the present invention.

Referring now to the drawings and to FIG. 1 in particular, a cross-sectional schematic representation of electrochromic device 100 is shown, which generally comprises first substrate 112 having a front surface 112A and a rear surface 112B, second substrate 114 having a front surface 114A and a rear surface 114B, and chamber 116 for containing electrochromic medium 124. It will be understood that electrochromic device 100 may comprise, for illustrative purposes only, a mirror, a window, a display device, a contrast enhancement filter, or the like. It will be further understood that FIG. 1 is merely a schematic representation of electrochromic device 100. As such, some of the components have been distorted from their actual scale for pictorial clarity. Indeed, numerous other electrochromic device configurations are contemplated for use, including those disclosed in U.S. Pat. No. 5,818,625 entitled "Electrochromic Reanrew Mirror Incorporating A Third Surface Metal Reflector" and U.S. application Ser. No. 09/343,345 entitled "Electrode Design For Electrochromic Devices," both of which are incorporated herein by reference in their entirety.

First substrate 112 may be fabricated from any one of a number of materials that are transparent or substantially transparent in the visible region of the electromagnetic spectrum, such as, for example, borosilicate glass, soda lime glass, float glass, natural and synthetic polymeric resins or plastics including Topas®, which is commercially available from Ticona of Summit, N.J. First substrate 112 is preferably fabricated from a sheet of material having a thickness ranging from approximately 0.5 millimeters (mm) to approximately 12.7 mm. Of course, the thickness of the substrate will depend largely upon the particular application of the electrochromic device. While particular substrate materials have been disclosed, for illustrative purposes only, it will be understood that numerous other substrate materials are likewise contemplated for use—so long as the materials are at least substantially transparent and exhibit appropriate physical properties which will enable them to operate effectively in conditions of intended use. Indeed, electrochromic devices in accordance with the present invention can be, during normal operation, exposed to extreme temperatures as well as exposed to substantial ultraviolet radiation, emanating primarily from the sun.

Second substrate 114 can be fabricated from similar materials as that of first substrate 112. However, if the electrochromic device is a mirror, then the requisite of substantial transparency is not necessary. As such, second substrate 114 may, alternatively, comprise polymers, metals, glass, ceramics, or other similar materials. Second substrate 114 is preferably fabricated from a sheet of glass having a thickness ranging from approximately 0.5 mm to approximately 12.7 mm. If first and second substrates 112 and 114, respectively, are fabricated from sheets of glass, then the glass can optionally be tempered or strengthened by thermal or chemical means prior to or subsequent to being coated with layers of electrically conductive material (118 and 120).

One or more layers of electrically conductive material 118 are associated with rear surface 112B of first substrate 112. These layers serve as an electrode for the electrochromic device. Electrically conductive material 118 is desirably a material that: (a) is substantially transparent in the visible region of the electromagnetic spectrum; (b) bonds reasonably well to first substrate 112; (c) maintains this bond when associated with a sealing member; (d) is generally resistant to corrosion from materials contained within the electrochromic device or the atmosphere; and (e) exhibits minimal diffusion or specular reflectance as well as sufficient electrical conductance. It is contemplated that electrically conductive material 118 may be fabricated from fluorine-doped tin oxide (FTO), for example TEC glass, which is commercially available from Liibbey Owens-Ford-Co., of Toledo, Ohio, indium-doped tin oxide (ITO), doped zinc oxide, or other materials known in the art.

Electrically conductive material 120 is preferably associated with front surface 114A of second substrate 114, and is operatively bonded to electrically conductive material 118 by sealing member 122. As can be seen in FIG. 1, once bonded, sealing member 122 and the juxtaposed portions of electrically conductive materials 118 and 120 serve to define the inner peripheral geometry of chamber 116.

Electrically conductive material 120 may vary depending upon the intended use of the electrochromic device. For example, if the electrochromic device is a mirror, then the material may comprise a transparent conductive coating similar to electrically conductive material 118 (in which case a reflector is associated with rear surface 114B (not shown) of second substrate 114). Alternatively, electrically conductive material 120 may comprise a layer of reflective material in accordance with the teachings of the above-referenced '625 patent. In this case, electrically conductive material 120 is associated with front surface 114A of second substrate 114. Typical coatings for this type of reflector include chromium, rhodium, ruthenium, silver, silver alloys, and combinations thereof.

Sealing member 122 may comprise any material that is capable of being adhesively bonded to the electrically conductive materials 118 and 120 to, in turn, seal chamber 116 so that one or more components of electrochromic medium 124 do not inadvertently leak out of the chamber. As is shown in dashed lines in FIG. 1, it is also contemplated that the sealing member extend all the way to rear surface 112B and front surface 114A of their respective substrates. In such an embodiment, the layers of electrically conductive material 118 and 120 may be partially removed where the sealing member 122 is positioned. If electrically conductive materials 118 and 120 are not associated with their respective substrates, then sealing member 122 preferably bonds well to glass. It will be understood that sealing member 122 can be fabricated from any one of a number of materials including, for example, those disclosed in U.S. Pat. Nos.: 4,297,401; 4,418,102; 4,695,490; 5,596,023; 5,596,024; 4,297,401; and U.S. patent application Ser. No. 09/158,423 entitled "Improved Seal For Electrochromic Devices," all of which are incorporated herein by reference.

Electrochromic medium 124 generally comprises one or more cathodic electrochromic materials, and one or more anodic electrochromic materials which are at least partially dissolved in one or more solvents. However, a hybrid electrochromic medium is likewise contemplated for use. In a hybrid electrocbromic medium, an electrochromic material can be applied (in a solid form) to its respective electrically conductive material. For example, tungsten oxide ($WO_3$) can be applied onto the surface of a conventional electrically conductive material. The term "electrochromic" will be defined herein, regardless of its ordinary meaning, as a material that has a change in its extinction coefficient at one or more wavelengths upon exposure to a particular electrical potential difference. While the anodic and cathodic materials have been disclosed as being "electrochromic," it is likewise contemplated that one of the anodic or cathodic materials can be merely "electroactive." The term "electroactive" will be defined herein, regardless of its ordinary meaning, as a material that undergoes a modification in its oxidation state upon exposure to a particular electrical potential difference.

In addition, more than one anodic and cathodic material can be combined to give a pre-selected color as described in U.S. Pat. No. 6,020,987 entitled "Improved Electrochromic Medium Capable of Producing A Pre-Selected Color," which is incorporated herein by reference in its entirety.

It will be understood that the electrochromic materials disclosed in the present invention may be combined or linked by a bridging unit in accordance with the teachings of International Application Serial No. PCT/EP97/00499 entitled "Electrochromic System."

It will be further understood that the electrochromic materials disclosed in the present invention may also be "tied" into gelatinous media in accordance with the teachings of U.S. Pat. No. 5,910,854 entitled "Electrochromic Polymeric Solid Films, Manufacturing Electrochromic Devices Using Such Solid Films, And Processes For Making Such Solid Films and Devices," which is incorporated herein by reference.

Electrochromic medium 124 may also comprise any one of a number of gelatinous materials including those disclosed in U.S. Pat. No. 5,679,283; U.S. Pat. No. 5,888,431; and U.S. Pat. No. 5,928,572 which are issued to Tonar et al., entitled "Electrochromic Layer And Devices Comprising Same," and incorporated herein by reference in their entirety as well as the previously referenced and incorporated '854 patent.

Cathodic materials may include, metal oxides, such as $WO_3$, polymeric viologens, bipyridinyl based viologens, such as methyl viologen tetrafluoroborate, octyl viologen tetrafluoroborate, phenylpropyl viologen tetrafluoroborate, and hydroxyethyl viologen tetrafluoroborate. It will be understood that the preparation of the above-identified viologens is well known in the art. While specific cathodic materials have been provided, for illustrative purposes only, numerous other conventional cathodic materials are likewise contemplated for use including, but by no means limited to, those disclosed in U.S. Pat. No. 4,902,108, which is incorporated herein by reference in its entirety. Indeed, the only contemplated limitation relative to the cathodic material is that it should not adversely affect the electrochromic performance of device 100.

In accordance with the present invention, anodic electrochromic materials may include those represented by the formula:

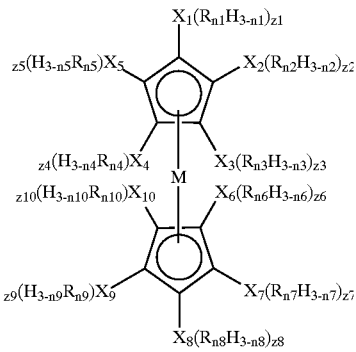

wherein M comprises a transition metal; wherein $X_1$–$X_{10}$ are the same or different and comprise C, Si, or H; wherein $R_{n1}$–$R_{n10}$ are the same or different and comprise O, C, or a straight or branched alkyl, aryl, alkaryl, or aralkyl group containing approximately 1 to approximately 40 carbon atom(s), wherein the carbon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates; ketones; esters; and amides; ethers, including linear, cyclic, and polyethers; amines, including tertiary amines; alkenes; alkynes; and mixtures thereof; wherein $n_1$–$n_{10}$ are the same or different and comprise 0, 1, 2, or 3, and are the number of bonds between a given X and associated constituent(s) other than hydrogen; wherein $Z_1$–$Z_{10}$ are the same or different and comprise 0 or 1; and wherein $$\sum_{y=1}^{10} n_y \geq 7; \sum_{y=1}^{10} z_y \geq 7; \text{ or } \sum_{y=1}^{10} (n_y + z_y) \geq 9.$$

Table I provides the summation values of "n" and "z" for numerous materials disclosed herein:

TABLE I

| Material | Σn | Σz |
|---|---|---|
| Ferrocene | 0 | 0 |
| 1,1'-di-t-butylferrocene | 6 | 2 |
| 1,1',3,3'-tetra-t-butylferrocene | 12 | 4 |
| 1-triethylammonium-6-(tetra-t-butylferrocenyl)hexane | 13 | 5 |
| 1,1',2,2',3,3',4,4'-octamethylferrocene | 0 | 8 |
| di(methylpentanoate)octamethylferrocene | 2 | 10 |
| 1,1'-diethyl-3,3'-di-t-butylferrocene | 8 | 4 |
| 1,1'-dimethylferrocene | 0 | 2 |
| 1,1',2,2',3,3',4,4',5,5'-decamethylferrocene | 0 | 10 |

In an alternative form of expression, anodic electrochromic materials of the present invention may include those represented by the formula:

wherein Mc is a metallocene; wherein E is either C or Si; wherein E is bound to a carbon atom contained within a cyclopentadienyl ring of the metallocene; wherein y designates 1 through 10 carbon atom positions of the cyclopentadienyl rings of the metallocene; wherein R is the same or different and comprises O, C, or a straight or branched alkyl, aryl, alkaryl, or aralkyl group containing approximately 1 to approximately 40 carbon atom(s), wherein the carbon atom (s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates; ketones; esters; and amides; ethers, including linear, cyclic, and polyethers; amines, including tertiary amines; alkenes; alkynes; and mixtures thereof; wherein n is the same or different and comprises 0, 1, 2, or 3, and are the number of bonds E to R, other than hydrogen, for each cyclopentadienyl position y; wherein z is 0 or 1, and if z is 0, then $(ER_nH_{3-n})$ is defined as hydrogen; and wherein $$\sum_{y=1}^{10} n_y \geq 7; \sum_{y=1}^{10} z_y \geq 7; \text{ or } \sum_{y=1}^{10} (n_y + z_y) \geq 9.$$

For purposes of the present disclosure, anodic electrochromic materials may also comprise substituted metallocenes represented by the formula:

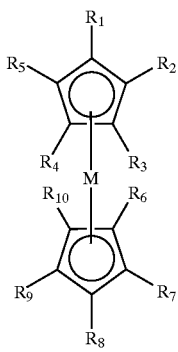

wherein $R_1$–$R_{10}$ are the same or different and at least three of $R_1$–$R_{10}$ are the same or different and comprise a straight or branched alkyl, aryl, alkaryl, or aralkyl group containing approximately 1 to approximately 40 carbon atom(s); and/or a silyl or siloxyl group containing approximately 1 to approximately 40 silicon atom(s), wherein the carbon or silicon atom(s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates; carbamates; ketones; esters; and amides; ethers, including linear, cyclic, and polyethers, amines, including tertiary amines, alkenes; alkynes; and mixtures thereof; wherein any remainder of $R_1$–$R_{10}$ comprise H; and wherein M comprises a transition metal such as iron, ruthenium, etc.

As will be shown in the experiments below, the above-provided constituents can decrease the rate of undesirable side reactions by, among other things, blocking access to the metal center of the metallocene, thereby increasing its stability. Increasing stability of the anodic electrochromic material is extremely important inasmuch as electrochromic windows and/or mirrors can be, during normal operation, routinely exposed to extreme high and low temperatures as well as ultraviolet radiation. Continuous exposure to these environments can cause the anodic electrochromic material, among other materials, to degrade or otherwise modify from its original chemical structure and alter its very important color characteristics. In particular, upon degradation the anodic electrochromic material can develop residual color (during the high transmittance state) and/or become tinted with an undesirable color (during the low transmittance state), either of which can be especially problematic for highly visible electrochromic windows and mirrors. As will be discussed below, the degree of coloration can be expressed in terms of a material's L*a*b* coordinate data.

While increased thermal and/or ultraviolet stability is an important benefit associated with the present invention, an additional realized benefit is that these anodic electrochromic materials can exhibit lower redox potentials. The lower redox potentials of these materials enables a device to operate at a lower applied potential than their non-substituted or simple substituted counterparts. Moreover, the lower redox potentials of these anodic electrochromic materials further increases their compatibility and/or utilization with color-stabilized buffer systems which are disclosed in U.S. application Ser. No. 09/377,455 entitled "Color-Stabilized Electrochromic Devices."

Specific examples of some suitable anodic electrochromic materials include:

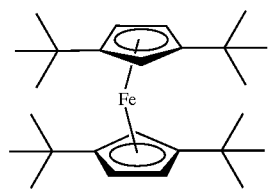

Tetra-t-butylferrocene

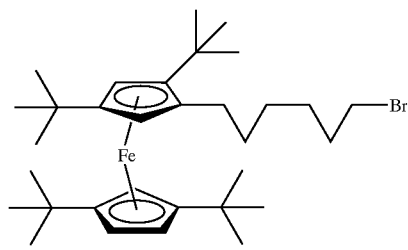

1-Bromo-6-(tetra-t-butylferrocenyl)hexane

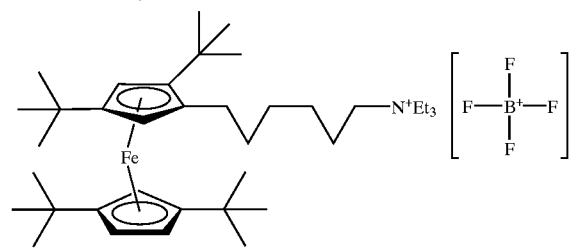

1-Triethylammonium-6-(tetra-t-butylferrocenyl)hexane BF$_4$

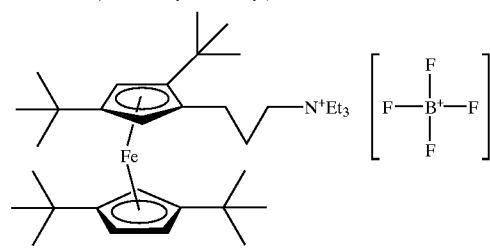

1-Triethylammonium-3-(tetra-t-butylferrocenyl)propane BF$_4$

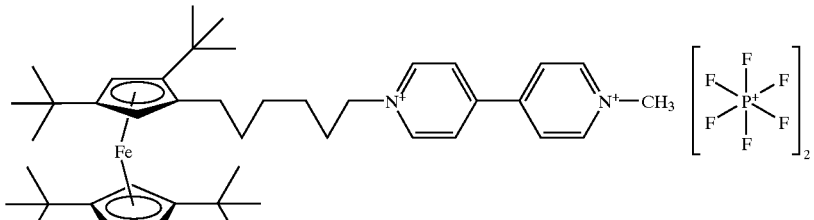

Tetra-t-butylferrocenehexylmethylviologen [PF$_6$]$_2$

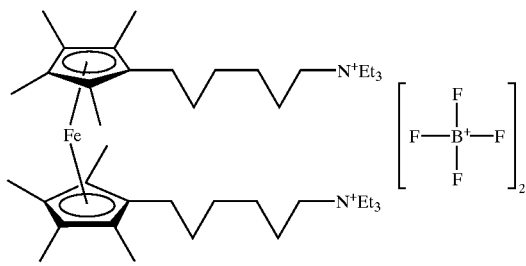

Di(triethylammoniumhexyl)octamethylferrocene

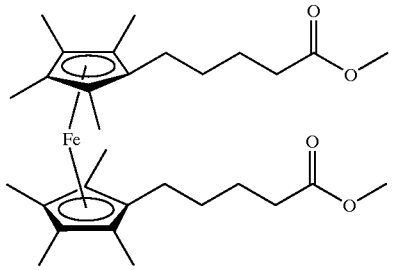

Di(methylpentanoate)octamethylferrocene

It will be understood that information regarding the commercial availability and/or preparation of anodic electrochromic materials of the present invention can be found in U.S. application Ser. No. 09/377,455 entitled "Color-Stabilized Electrochromic Devices" and U.S. application Ser. No. 09/454,043 entitled "Anodic Electrochromic Materials Having a Solublizing Moiety" both of which are incorporated by reference herein including the references cited therein.

While specific anodic electrochromic materials have been disclosed herein, numerous other anodic electrochromic materials that would be known to those having ordinary skill in the art having the present disclosure before them are likewise contemplated for use.

For illustrative purposes only, the concentration of the anodic and cathodic electrochromic materials can range from approximately 1 millimolar (mM) to approximately 500 mM and more preferably from approximately 5 mM to approximately 50 mM. While particular concentrations of the anodic as well as cathodic electrochromic materials have been provided, it will be understood that the desired concentration may vary greatly depending upon the geometric configuration of the chamber containing electrochromic medium 124, and/or other properties of the medium such as, but not limited to, viscosity, dielectric constant, etc.

For purposes of the present disclosure, electrochromic medium 124 may comprise any one of a number of common, commercially available solvents including 3-methylsulfolane, sulfolane, glutaronitrile, dimethyl sulfoxide, dimethyl formamide, acetonitrile, tetraglyme and other polyethers, alcohols such as ethoxyethanol, nitriles such as 3-hydroxypropionitrile, 2-methylglutaronitrile, ketones including 2-acetylbutyrolactone, cyclopentanone, cyclic esters including beta-propiolactone, gamma-butyrolactone, gamma-valerolactone, propylene carbonate, ethylene carbonate and homogenous mixtures of the same. While specific solvents have been disclosed as being associated with the electrochromic medium, numerous other solvents that would be known to those having ordinary skill in the art having the present disclosure before them are likewise contemplated for use.

In addition, the electrochromic medium may comprise other materials, such as light absorbers, light stabilizers, thermal stabilizers, antioxidants, tint providing agents, and mixtures thereof Suitable UV-stabilizers may include: the material ethyl-2-cyano-3,3-diphenyl acrylate, sold by BASF of Parsippany, N.Y. under the trademark Uvinul N-35 and by Aceto Corp., of Flushing, N.Y. under the trademark Viosorb 910; the material (2-ethylhexyl)-2-cyano-3,3-diphenyl acrylate, sold by BASF under the trademark Uvinul N-539; the material 2-(2'-hydroxy-4'-methylphenyl)benzotriazole, sold by Ciba-Geigy Corp. under the trademark Tinuvin P; the material 3-[3-(2H-benzotriazole-2-yl)-5-(1,1-dimethylethyl)-4-hydroxyphenyl]propionic acid pentyl ester prepared from Tinuvin 213, sold by Ciba-Geigy Corp., via conventional hydrolysis followed by conventional esterification (hereinafter "Tinuvin PE"); the material 2-hydroxy-4-methoxybezophenone sold by American Cyanamid under the trademark Cyasorb UV 9; and the material 2-ethyl-2'-ethoxyalanilide sold by Sandoz Color & Chemicals under the trademark Sanduvor VSU—to name a few.

Electrochromic devices having as a component part an above-identified electrochromic medium can be used in a wide variety of applications wherein, under normal operation, the transmitted or reflected light can be modulated—the skill of which is well known in the art. Such devices include rear-view mirrors for vehicles; windows for the exterior of a building, home or vehicle; skylights for buildings including tubular light filters; windows in office or room partitions; display devices, contrast enhancement filters for displays; light filters for photographic devices and light sensors; and indicators for power cells as well as primary and secondary electrochemical cells.

In support of the present invention, Experiment Nos. A1–A9 were conducted wherein electrochromic devices were prepared using nine different anodic electrochromic materials. In particular, the anodic electrochromic material for Experiment No. A1 comprised non-substituted ferrocene, the anodic electrochromic materials for Experiment Nos. A2 and A8 comprised different simple substituted ferrocenes, and the anodic electrochromic materials for Experiment Nos. A3–A7 and A9 comprised appreciably substituted ferrocenes. As will be discussed in detail below, the devices were grouped into different sets and each set was exposed to different thermal and/or ultraviolet radiation, which were tested at predetermined time intervals for color stability.

In discussing colors it is useful to refer to the Commission Internationale de l'Eclairage's (CIE) 1976 CIELAB Chromaticity Diagram (commonly referred to the L*a*b* chart). The technology of color is relatively complex, but a fairly comprehensive discussion is given by F. W. Billmeyer and M. Saltzman in Principles of Color Technology, $2^{nd}$ Ed., J. Wiley and Sons Inc. (198 1), and the present disclosure, as it relates to color technology and terminology generally follows that discussion. On the L*a*b* chart, L* defines lightness, a* denotes the red/green value and b* denotes the yellow/blue value. Each of the electrochromic media has an absorption spectra at each particular voltage that may be converted into a three number designation, their L*a*b* values. Color change is calculated by importing L*a*b* values into the following formula:

$$\Delta E = SQRT((L_t^* - L_0^*)^2 + (a_t^* - a_0^*)^2 + (b_t^* - b_0^*)^2)$$

wherein

ΔE is the color change;

SQRT is the square root operation;

Subscript "0" is an initial value (for L*, a*, or b*); and

Subscript "t" is a value after a given amount of time (for L*, a*, or b*).

EXPERIMENT NOS. A1–A9

In Experiment Nos. A1–A9 nine different media were prepared by dissolving the following materials in propylene carbonate (PC) at a concentration of 50 mM:

| Experiment No. | Material |
| --- | --- |
| A1 | ferrocinium tetrafluoroborate |
| A2 | 1,1'-di-t-butylferrocinium tetrafluoroborate |
| A3 | 1,1',3,3'-tetra-t-butylferrocinium tetrafluoroborate |
| A4 | 1-triethylammonium-6-(tetra-t-butylferrocinium)hexane ditetrafluoroborate |
| A5 | 1,1',2,2',3,3',4,4'-octamethylferrocinium tetrafluorobrate |
| A6 | di(methylpentanoate)octamethylferrocinium tetrafluoroborate |
| A7 | 1,1'-diethyl-3,3'-di-t-butylferrocinium tetrafluoroborate |
| A8 | 1,1'-dimethylferrocinium tetrafluoroborate |
| A9 | 1,1',2,2',3,3',4,4',5,5'-decamethylferrocinium tetrafluroborate |

The above-identified ferrocinium derivatives were used in the following experiments, as opposed to ferrocenes, due to their favorable solubility in PC. In addition, the ferrocinium derivatives provided for more rigorous testing parameters inasmuch as the cyclopentadienyl-metal bond length is increased upon oxidation, thereby enabling easier access to the metal center for adverse chemical reactions and/or degradation. The above-identified ferrocinium derivatives can be prepared in accordance with the teaching of U.S. application Ser. No. 09/377,455 entitled "Color Stabilized Electrochromic Devices" and Cunningham, K. L.; McMillin, D. R. *Polyhedron*, 1996, 15(10), 1673–1675.

The media from Experiment Nos. A1–A9 were associated with two sets of electrochromic window parts for testing. Specifically, each window comprised two 2×5 inch substrates, both of which were coated with generally clear, conductive indium-doped tin oxide on their respective inner surfaces. The substrates were spaced 250 microns apart for accommodating the medium which was vacuum filled via conventional means. The first set of windows were stored in an oven at 85 degrees centigrade (See FIG. 2). The second set of windows were exposed to static ultraviolet radiation (See FIG. 3). For each of the experimental sets, L*a*b* data were collected at predetermined intervals, which were then converted into an average color change value, the results of which are provided in FIGS. 2 and 3. It will be understood that the color change was an average of the above-identified "ΔE" value for two electrochromic devices.

Figure 2:
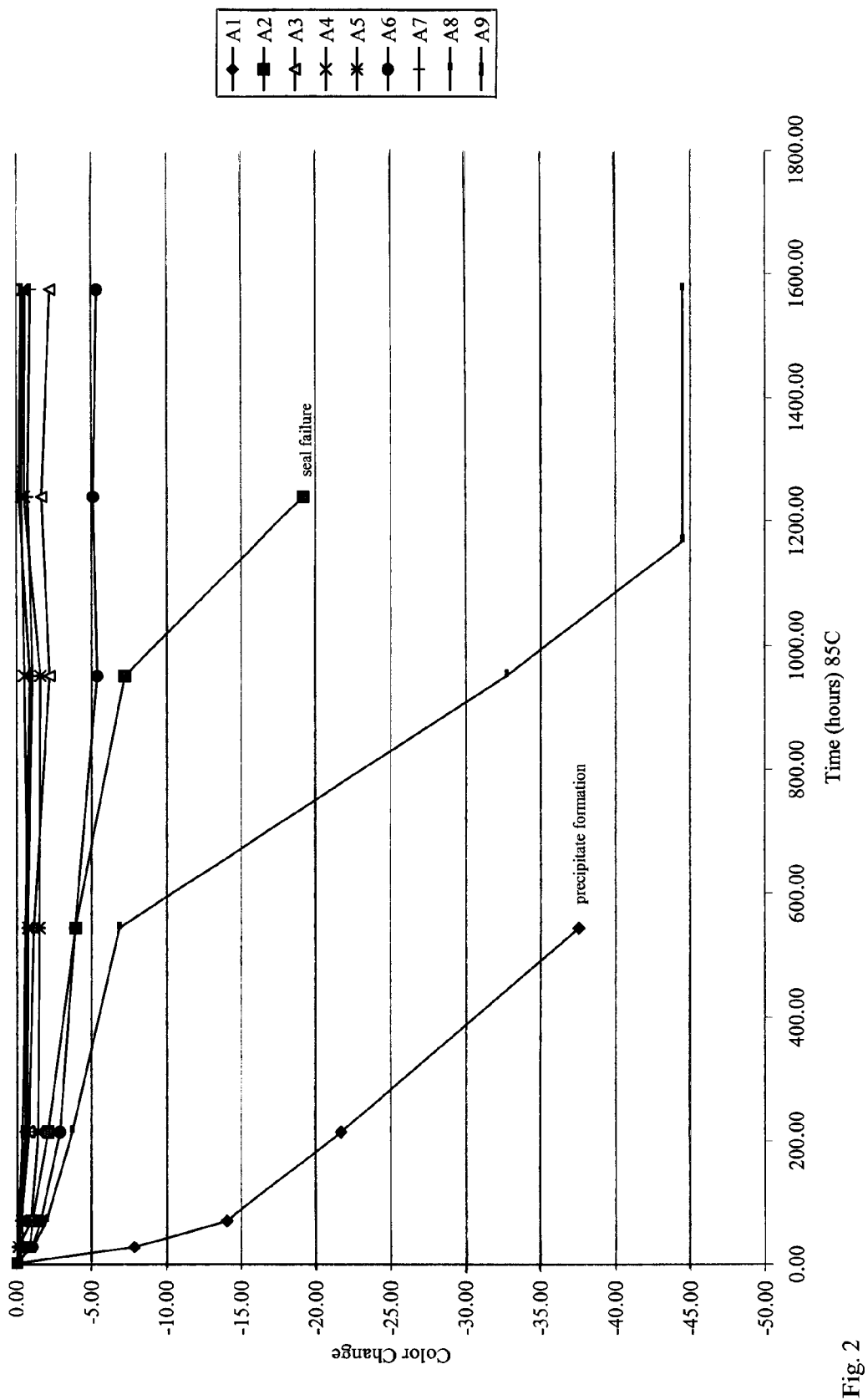
FIG. 2 of the drawings is a two-dimensional plot showing the average color change as a function of exposure time at 85 degrees centigrade for Experiments A1–A9.
Figure 3:
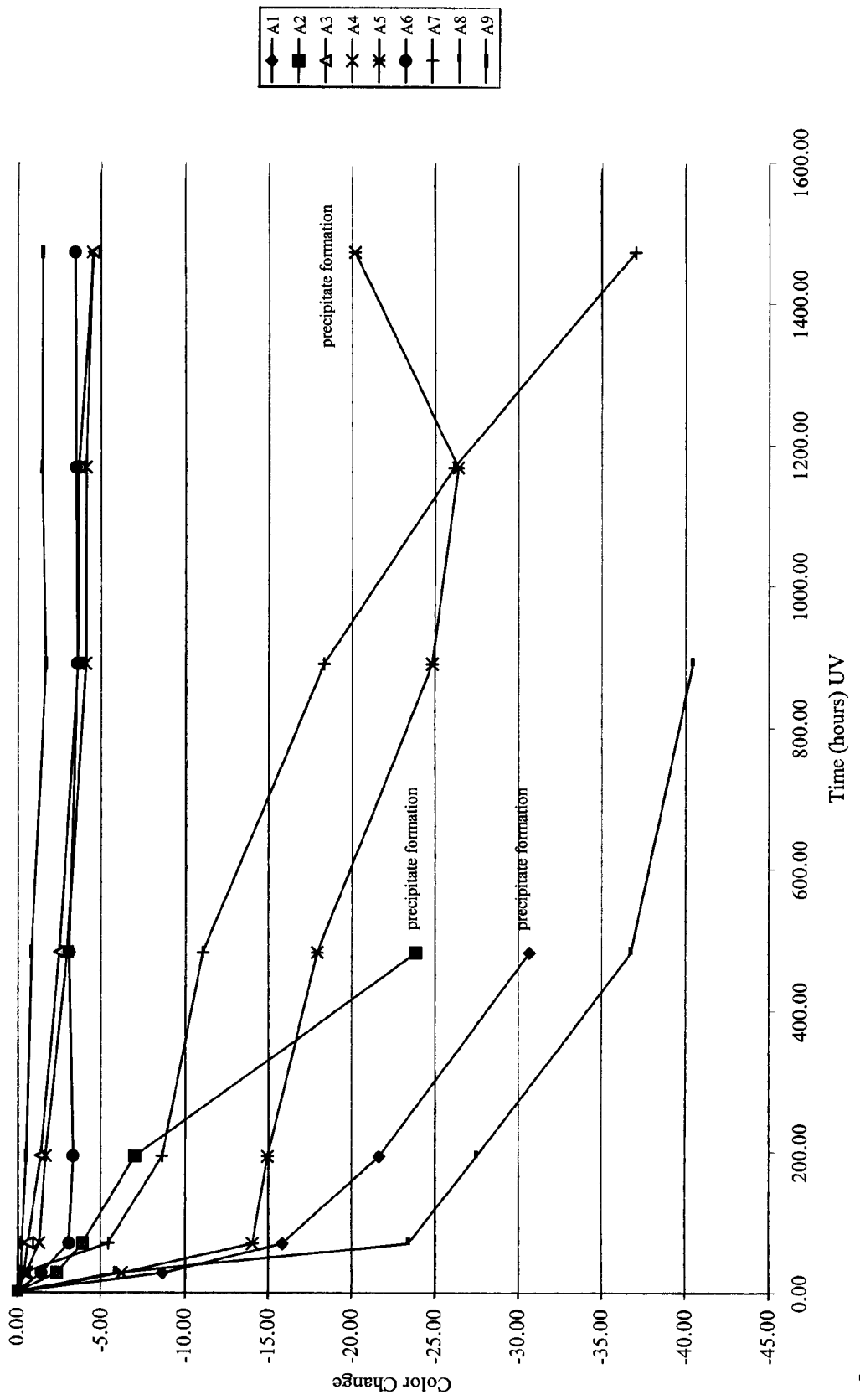
FIG. 3 of the drawings is a two-dimensional plot showing the average color change as a function of exposure time to static ultraviolet radiation for Experiments A1–A9.

As is best shown in FIG. 2, the media comprising materially substituted metallocenes are substantially more stable than the media comprising simple or non-substituted metallocenes. In fact, the media of Experiment Nos. A1, A2, and A8 experienced substantial changes in color as is evident by their relatively large negative slope as compared to the extremely small negative slopes of the remainder of the Experiments. In addition, the media of experiments A1 and A2 became non operative as a result of precipitate formation and seal failure, respectively. As is shown in FIG. 3, similar favorable results were obtained for windows exposed to static ultraviolet radiation.

As can be seen from the above-provided experiments, the incorporation of a metallocene associated with stability-enhancing constituents improves the color stability of an electrochromic medium while being exposed to thermal and/or ultraviolet radiation. It will be understood that the stability of anodic electrochromic materials can be further enhanced in accordance with the teaching of U.S. application Ser. No. 09/377,455 entitled "Color Stabilized Electrochromic Devices."

While the invention has been described in detail herein in accordance with certain preferred embodiments thereof, many modifications and changes therein may be effected by those skilled in the art. Accordingly, it is our intent to be limited only by the scope of the appending claims and not by way of details and instrumentalities describing the embodiments shown herein.

What is claimed is:

1. An electrochromic device, comprising:

a first substantially transparent substrate having an electrically conductive material associated therewith;

a second substrate having an electrically conductive material associated therewith; and an electrochromic medium contained within a chamber positioned between the first and second substrates which comprises a material represented by the formula:

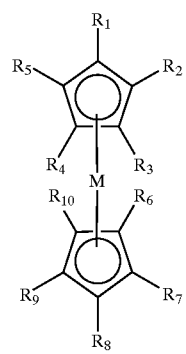

wherein $R_1$–$R_{10}$ are the same or different and at least three of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

2. The electrochromic device according to claim 1, wherein $R_1$–$R_{10}$ are the same or different and at least four of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

3. The electrochromic device according to claim 2, wherein at least two of $R_1$–$R_5$ are the same or different and at least two of $R_6$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof.

4. The electrochromic device according to claim 3, wherein two of $R_1$–$R_5$ are the same or different and two of $R_6$–$R_{10}$ are the same or different and comprise a straight or branched alkyl, aryl, alkaryl, or aralkyl group containing approximately 1 to approximately 40 carbon atom(s), wherein the carbon atom(s) may be a linking group to one or more ammonium constituents.

5. The electrochromic device according to claim 4, wherein one of $R_1$–$R_5$ is linked to an ammonium constituent.

6. The electrochromic device according to claim 1, wherein $R_1$–$R_{10}$ are the same or different and at least four of $R_1$–$R_{10}$ are the same or different and comprise a straight or branched alkyl, aryl, alkaryl, or aralkyl group containing 1 to 40 carbon atoms, and/or a silyl or siloxyl group containing 1 to 40 silicon atoms, wherein the carbon or silicon atoms may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

7. The electrochromic device according to claim 6, wherein M comprises Fe.

8. The electrochromic device according to claim 1, wherein M comprises Fe.

9. The electrochromic device according to claim 1, further comprising a cross-linked polymer matrix or a free standing gel.

10. The electrochromic device according to claim 1, wherein the electrochromic medium comprises 1,1',2,2',3,3',4,4',5,5'-decamethylferrocene.

11. The electrochromic device according to claim 10, wherein the electrochromic medium further comprises 1,1',2,2',3,3',4,4',5,5'-decamethylferrocinium tetrafluoroborate.

12. The electrochromic device according to claim 1, wherein the electrochromic medium comprises 1,1',2,2',3,3',4,4',5,5'-decamethylferrocinium tetrafluoroborate.

13. An electrochromic device, comprising:
    a first substantially transparent substrate having an electrically conductive material associated therewith;
    a second substrate having an electrically conductive material associated therewith; and
    an electrochromic medium contained within a chamber positioned between the first and second substrates which comprises a metallocene, wherein the metallocene comprises at least three substituents which serve to increase stability of the metallocene relative to the stability of the metallocene without the at least three substituents.

14. The electrochromic device according to claim 13, wherein the metallocene comprises a substituted ferrocene.

15. The electrochromic device according to claim 13, wherein the at least three substituents are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof.

16. An electrochromic device, comprising: a first substantially transparent substrate having an electrically conductive material associated therewith; a second substrate having an electrically conductive material associated therewith; an electrochromic medium contained within a chamber positioned between the first and second substrates which comprises a metallocene, wherein the metallocene comprises at least four substituents which serve to increase stability of the metallocene relative to the stability of the metallocene without the at least four substituents.

17. An electrochromic medium for use in an electrochromic device, comprising: a material represented by the formula:

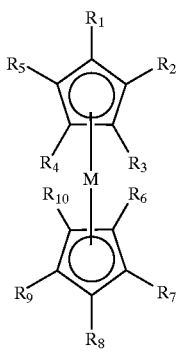

wherein $R_1$–$R_{10}$ are the same or different and at least three of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

18. The electrochromic medium according to claim 17, wherein $R_1$–$R_{10}$ are the same or different and at least four of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

19. The electrochromic medium according to claim 18, wherein at least two of $R_1$–$R_5$ are the same or different and at least two of $R_6$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof.

20. The electrochromic medium according to claim 19, wherein two of $R_1$–$R_5$ are the same or different and two of $R_6$–$R_{10}$ are the same or different and comprise a straight or branched alkyl, aryl, alkaryl, or aralkyl group containing approximately 1 to approximately 40 carbon atom(s), wherein the carbon atom(s) may be a linking group to one or more ammonium constituents.

21. The electrochromic medium according to claim 20, wherein one of $R_1$–$R_5$ is linked to an ammonium constituent.

22. The electrochromic medium according to claim 17, wherein $R_1$–$R_{10}$ are the same or different and at least four of $R_1$–$R_{10}$ are the same or different and comprise a straight or branched alkyl, aryl, alkaryl, or aralkyl group containing 1 to 40 carbon atoms, and/or a silyl or siloxyl group containing 1 to 40 silicon atoms, wherein the carbon or silicon atoms may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

23. The electrochromic medium according to claim 22, wherein M comprises Fe.

24. The electrochromic medium according to claim 17, further comprising a cross-linked polymer matrix or a free standing gel.

25. An electrochromic medium for use in an electrochromic device, comprising: a metallocene, wherein the metallocene comprises at least three substituents which serve to increase stability of the metallocene relative to the stability of the metallocene without the at least three substituents.

26. The electrochromic medium according to claim 25, wherein the metallocene comprises a substituted ferrocene.

27. The electrochromic medium according to claim 25, wherein the at least three substituents are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof.

28. A material for use in an electrochromic device represented by the formula:

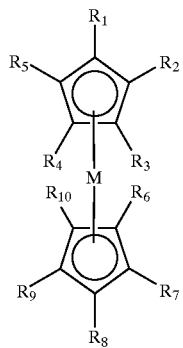

wherein $R_1$–$R_{10}$ are the same or different and at least three of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

29. The material according to claim 28, wherein $R_1$–$R_{10}$ are the same or different and at least four of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

30. The material according to claim 29, wherein at least two of $R_1$–$R_5$ are the same or different and at least two of $R_6$–$R_{10}$ are the same or different and comprise a straight or branched alkyl, aryl, alkaryl, or aralkyl group containing approximately 1 to approximately 40 carbon atom(s); and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates; carbamates; ketones; esters; and amides; ethers, including polyethers; amines, including tertiary amines; alkenes; alkynes; and mixtures thereof.

31. The material according to claim 30, wherein two of $R_1$–$R_5$ are the same or different and two of $R_6$–$R_{10}$ are the same or different and comprise a straight or branched alkyl, aryl, alkaryl, or aralkyl group containing approximately 1 to approximately 40 carbon atom(s), wherein the carbon atom(s) may be a linking group to one or more ammonium constituents.

32. The material according to claim 31, wherein one of $R_1$–$R_5$ is linked to an ammonium constituent.

33. The material according to claim 28, wherein $R_1$–$R_{10}$ are the same or different and at least four of $R_1$–$R_{10}$ are the same or different and comprise a straight or branched alkyl, aryl, alkaryl, or aralkyl group containing 1 to 40 carbon atoms, and/or a silyl or siloxyl group containing 1 to 40 silicon atoms, wherein the carbon or silicon atoms may be a linking group to, or part of, one or more functional groups comprising nitrites; nitro constituents; sulfoxides; sulfonates; phosphonium constituents; phosphonates; phospho- nites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof, wherein any remainder of $R_1$–$R_{10}$ comprise H; and wherein M comprises a transition metal in any available oxidation state.

34. The material according to claim 33, wherein M comprises Fe.

35. An electrochromic device, comprising:

a first substantially transparent substrate having an electrically conductive material associated therewith;

a second substrate having an electrically conductive material associated therewith; and an electrochromic medium contained within a chamber positioned between the first and second substrates which comprises a material represented by the formula:

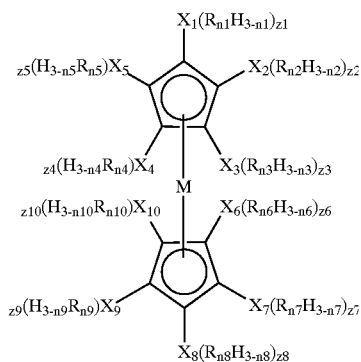

wherein M comprises a transition metal in any available oxidation state; wherein $X_1$–$X_{10}$ are the same or different and comprise C, Si, or H; wherein $R_{n1}$–$R_{n10}$ are the same or different and comprise O, C, or a straight or branched alkyl, aryl, alkaryl, or aralkyl group containing approximately 1 to approximately 40 carbon atom(s), wherein the carbon atom(s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein $n_1$–$n_{10}$ are the same or different and comprise 0, 1, 2, or 3, and are the number of bonds between a given X and associated constituent(s) other than hydrogen; wherein $Z_1$–$Z_{10}$ are the same or different and comprise 0 or 1;

and wherein $$\sum_{y=1}^{10} n_y \geq 7; \sum_{y=1}^{10} z_y \geq 7; \text{ or } \sum_{y=1}^{10} (n_y + z_y) \geq 9.$$

36. The electrochromic device according to claim 35, wherein $$\sum_{y=1}^{10} n_y \geq 8; \quad \sum_{y=1}^{10} z_y \geq 8; \quad \text{or} \quad \sum_{y=1}^{10} (n_y + z_y) \geq 10.$$

37. An electrochromic medium for use in an electrochromic device, comprising: a material represented by the formula:

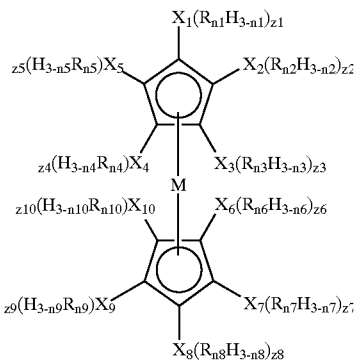

wherein M comprises a transition metal in any available oxidation state; wherein $X_1$–$X_{10}$ are the same or different and comprise C, Si, or H; wherein $R_{n1}$–$R_{n10}$ are the same or different and comprise O, C, or a straight or branched alkyl, aryl, alkaryl, or aralkyl group containing approximately 1 to approximately 40 carbon atom(s), wherein the carbon atom (s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof, wherein $n_1$–$n_{10}$ are the same or different and comprise 0, 1, 2, or 3, and are the number of bonds between a given X and associated constituent(s) other than hydrogen; wherein $Z_1$–$Z_{10}$ are the same or different and comprise 0 or 1;

and wherein $$\sum_{y=1}^{10} n_y \geq 7; \quad \sum_{y=1}^{10} z_y \geq 7; \quad \text{or} \quad \sum_{y=1}^{10} (n_y + z_y) \geq 9.$$

38. The electrochromic medium according to claim 37, wherein $$\sum_{y=1}^{10} n_y \geq 8; \quad \sum_{y=1}^{10} z_y \geq 8; \quad \text{or} \quad \sum_{y=1}^{10} (n_y + z_y) \geq 10.$$

39. A material for use in an electrochromic device represented by the formula:

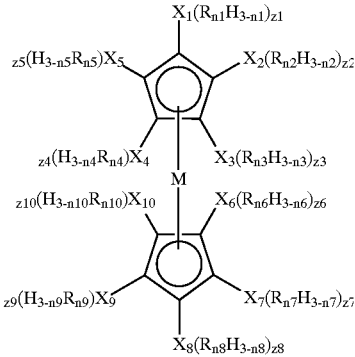

wherein M comprises a transition metal in any available oxidation state; wherein $X_1$–$X_{10}$ are the same or different and comprise C, Si, or H; wherein $R_{n1}$–$R_{n10}$ are the same or different and comprise O, C, or a straight or branched alkyl, aryl, alkaryl, or aralkyl group containing approximately 1 to approximately 40 carbon atom(s), wherein the carbon atom (s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein $n_1$–$n_{10}$ are the same or different and comprise 0, 1, 2, or 3, and are the number of bonds between a given X and associated constituent(s) other than hydrogen; wherein $Z_1$–$Z_{10}$ are the same or different and comprise 0 or 1;

and wherein $$\sum_{y=1}^{10} n_y \geq 7; \quad \sum_{y=1}^{10} z_y \geq 7; \quad \text{or} \quad \sum_{y=1}^{10} (n_y + z_y) \geq 9.$$

40. The material according to claim 39, wherein $$\sum_{y=1}^{10} n_y \geq 8; \quad \sum_{y=1}^{10} z_y \geq 8; \quad \text{or} \quad \sum_{y=1}^{10} (n_y + z_y) \geq 10.$$

41. An electrochromic device, comprising:
a first substantially transparent substrate having an electrically conductive material associated therewith;
a second substrate having an electrically conductive material associated therewith; and
an electrochromic medium contained within a chamber positioned between the first and second substrates which comprises a material represented by the formula:

$$Mc-(ER_nH_{3-n})_z^y$$

wherein Mc is a metallocene; wherein E is either C or Si; wherein E is bound to a carbon atom contained within a cyclopentadienyl ring of the metallocene; wherein y designates 1 through 10 carbon atom positions of the cyclopentadienyl rings of the metallocene; wherein R is the same or different and comprises O, C, or a straight or branched alkyl, aryl, alkaryl, or aralkyl group containing approximately 1 to approximately 40 carbon atom(s), wherein the carbon atom (s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein n is the same or different and comprises 0, 1, 2, or 3, and are the number of bonds E to R, other than hydrogen, for each cyclopentadienyl position y; wherein z is 0 or 1, and if z is 0, then $(ER_nH_{3-n})$ is defined as hydrogen;

and wherein $$\sum_{y=1}^{10} n_y \geq 7; \sum_{y=1}^{10} z_y \geq 7; \text{ or } \sum_{y=1}^{10} (n_y + z_y) \geq 9.$$

42. The electrochromic device according to claim 41, wherein $$\sum_{y=1}^{10} n_y \geq 8; \sum_{y=1}^{10} z_y \geq 8; \text{ or } \sum_{y=1}^{10} (n_y + z_y) \geq 10.$$

43. An electrochromic medium for use in an electrochromic device, comprising: a material represented by the formula:

$$Mc\text{---}(ER_nH_{3-n})_z^y$$

wherein Mc is a metallocene; wherein E is either C or Si; wherein E is bound to a carbon atom contained within a cyclopentadienyl ring of the metallocene; wherein y designates 1 through 10 carbon atom positions of the cyclopentadienyl rings of the metallocene; wherein R is the same or different and comprises O, C, or a straight or branched alkyl, aryl, alkaryl, or aralkyl group containing approximately 1 to approximately 40 carbon atom(s), wherein the carbon atom (s) may be a linking group to, or part of, one or more functional groups comprising nitriles; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein n is the same or different and comprises 0, 1, 2, or 3, and are the number of bonds E to R, other than hydrogen, for each cyclopentadienyl position y; wherein z is 0 or 1, and if z is 0, then $(ER_nH_{3-n})$ is defined as hydrogen;

and wherein $$\sum_{y=1}^{10} n_y \geq 7; \sum_{y=1}^{10} z_y \geq 7; \text{ or } \sum_{y=1}^{10} (n_y + z_y) \geq 9.$$

44. The electrochromic medium according to claim 43, wherein $$\sum_{y=1}^{10} n_y \geq 8; \sum_{y=1}^{10} z_y \geq 8; \text{ or } \sum_{y=1}^{10} (n_y + z_y) \geq 10.$$

45. An electrochromic device, comprising:
a first substantially transparent substrate having an electrically conductive material associated therewith;
a second substrate having an electrically conductive material associated therewith; and
an electrochromic medium which comprises a material represented by the formula:

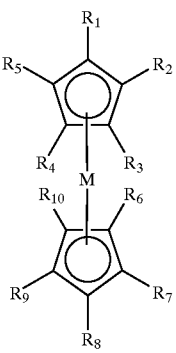

wherein $R_1$–$R_{10}$ are the same or different and at least three of $R_1$–$R_{10}$ are the same or different and comprise a straight or branched alkyl, aryl, alkaryl, or aralkyl group containing approximately 1 to approximately 40 carbon atom(s), and/or a silyl or siloxyl group containing approximately 1 to approximately 40 silicon atom(s), wherein the carbon or silicon atom(s) may be a linking group to, or part of, one or more functional groups comprising nitrites; nitro constituents; sulfoxides; sulfonates; phosphonium constituents; phosphonates; phosphonites; ammonium constituents; viologens, including bipyridinyl constituents; carbonyls, including carbonates, carbamates, ketones, esters, and amides; ethers, including polyethers; amines, including tertiary amines; alkenes; alkynes; and mixtures thereof; wherein any remainder of $R_1$–$R_{10}$ comprise H; and wherein M comprises a transition metal in any available oxidation state.

46. The electrochromic device according to claim 45, wherein the electrochromic medium comprises at least one of an anodic and cathodic material.

* * * * *